United States Patent
Grace et al.

(10) Patent No.: US 7,202,793 B2
(45) Date of Patent: Apr. 10, 2007

(54) APPARATUS AND METHOD OF MONITORING A SUBJECT AND PROVIDING FEEDBACK THERETO

(75) Inventors: Richard Grace, Pittsburgh, PA (US); Ellen M. Ayoob, Pittsburgh, PA (US)

(73) Assignee: Attention Technologies, Inc., Pittsburgh, PA (US)

( * ) Notice: Subject to any disclaimer, the term of this patent is extended or adjusted under 35 U.S.C. 154(b) by 853 days.

(21) Appl. No.: 10/269,508

(22) Filed: Oct. 11, 2002

(65) Prior Publication Data

US 2004/0070509 A1 Apr. 15, 2004

(51) Int. Cl.
*G08B 23/00* (2006.01)

(52) U.S. Cl. ........................ 340/576; 600/558

(58) Field of Classification Search ................ 340/576, 340/575, 573.1, 691.6, 692, 407.1; 434/238; 600/300, 558

See application file for complete search history.

(56) References Cited

U.S. PATENT DOCUMENTS

| | | | |
|---|---|---|---|
| 4,112,926 A * | 9/1978 | Schulman et al. ....... | 340/573.1 |
| 4,157,708 A | 6/1979 | Imura | |
| 4,220,142 A * | 9/1980 | Rosen et al. ................ | 340/575 |
| 4,919,534 A | 4/1990 | Reed | |
| 4,922,919 A | 5/1990 | Novack | |

(Continued)

FOREIGN PATENT DOCUMENTS

JP 52-54291 5/1977

(Continued)

OTHER PUBLICATIONS

Morimoto et al., "Pupil Detection and Tracking Using Multiple Light Sources", Image and Vision Computing 18, pp. 331-335 (2000).

(Continued)

*Primary Examiner*—Thomas Mullen
(74) *Attorney, Agent, or Firm*—Kirkpatrick & Lockhart Nicholson Graham LLP

(57) ABSTRACT

A device and method for monitoring a subject and providing feedback back to the subject that is pertinent to a behavior of the subject. The device includes a source of light having first and second wavelengths wherein the first wavelength does not equal the second wavelength; at least one image sensor producing a first signal indicative of reflected light having the first wavelength and a second signal indicative of reflected light having the second wavelength; a controller receiving the first and second signals and producing a third signal indicative of the first signal subtracted from the second signal; and an interface in communication with the controller providing informational content to the subject in response to the third signal, wherein the informational content is associated with a behavior of the subject. The method includes directing light having a first wavelength toward a subject; directing light having a second wavelength toward the subject, wherein the first wavelength does not equal the second wavelength; capturing a first image of light reflected by the subject having the first wavelength; capturing a second image of light reflected by the subject having the second wavelength; subtracting a signal indicative of the first image from a signal indicative of the second image and producing a third signal; and providing informational content to the subject in response to the third signal.

36 Claims, 6 Drawing Sheets

U.S. PATENT DOCUMENTS

| | | | |
|---|---|---|---|
| 4,953,111 A | | 8/1990 | Yamamoto et al. |
| 5,138,416 A | | 8/1992 | Brillson |
| 5,190,307 A | * | 3/1993 | Brown et al. ............... 340/576 |
| 5,402,109 A | * | 3/1995 | Mannik ...................... 340/575 |
| 5,598,145 A | * | 1/1997 | Shimotani et al. .......... 340/576 |
| 5,610,673 A | | 3/1997 | Rafal et al. |
| 5,689,241 A | | 11/1997 | Clarke, Sr. et al. |
| 5,691,693 A | * | 11/1997 | Kithil ........................ 340/439 |
| 5,729,619 A | * | 3/1998 | Puma ......................... 382/115 |
| 5,783,997 A | * | 7/1998 | Saitoh et al. ............... 340/576 |
| 5,801,390 A | | 9/1998 | Shiraishi |
| 6,082,858 A | * | 7/2000 | Grace et al. ................ 351/200 |
| 6,097,295 A | * | 8/2000 | Griesinger et al. ......... 340/576 |
| 6,130,421 A | | 10/2000 | Bechtel et al. |
| 6,166,815 A | | 12/2000 | Vali et al. |
| 6,366,207 B1 | * | 4/2002 | Murphy ...................... 340/576 |
| 6,496,724 B1 | * | 12/2002 | Levendowski et al. ..... 600/544 |
| 6,717,518 B1 | * | 4/2004 | Pirim et al. ................. 340/576 |

FOREIGN PATENT DOCUMENTS

| | | |
|---|---|---|
| JP | 2-138673 | 5/1990 |
| JP | 9-062828 | 3/1997 |

OTHER PUBLICATIONS

Yoshinobu Ebisawa, "Unconstrained Pupil Detectio Technique Using TwoLight Sources And The Image Difference Method," Faculty of Engineering, Shizuoka University, Johoku 3-5-1, Hamamatsu Shizuoka 432 Japan.

* cited by examiner

APPARATUS AND METHOD OF MONITORING A SUBJECT AND PROVIDING FEEDBACK THERETO

BACKGROUND OF THE INVENTION

1. Field of the Invention

The present invention is directed generally to an apparatus and method of monitoring a subject and providing feedback thereto and, more particularly, to an apparatus and method of monitoring a subject and providing informational feedback thereto.

2. Description of the Background

Driver drowsiness poses a major threat to roadway safety and the problem is particularly severe for commercial motor vehicle (CMV) drivers. There are approximately 1.6 million truck tractors and 3.6 million trailers used in the motor carrier industry today. CUT's are involved in approximately 200,000 crashes each year. A recent analysis of the problem size estimates that fatigue related crashes constitute: (1) 0.71% to 2.7% of all police reported crashes involving CUT's; (2) 3.2% to 7.6% of all fatalities associated with CUT crashes; and (3) 15% to 36% of all crashes fatal to the CUT driver. As is evident in these statistics, fatigue-related crashes tend to be severe. A typical fatigue related crash involves the CUT drifting off the roadway without brake application (run-off road crash). These crashes often occur early in the morning (between 2:00 AM and 6:00 AM) in light traffic conditions.

Thus, it may be desirable to have a drowsiness monitor and feedback device that promotes an understanding of fatigue, the potential consequences of driving while drowsy, and that provides guidance to drivers for managing fatigue. A common thread for addressing fatigue in any work environment is basic human physiology, in particular the need for sleep and the influence of natural circadian rhythms. If drivers are obtaining sufficient sleep, their alertness and performance will be optimized. If, however, drivers are receiving insufficient sleep, their alertness and performance will degrade accordingly.

A driver's alertness and corresponding performance levels also will cycle with the normal circadian rhythms. Performance degradation is most likely to occur during the natural circadian low points that occur for most people between 2:00 AM and 6:00 AM. A number of management structures have been proposed to promote fatigue management, safety and responsibility on the part of the driver. Fatigue, however, is illusive and often ill-defined, making management of fatigue qualitative and often based on indirect measures such as total time off-duty, etc. The problem is that decision-makers are often faced with too few facts and too many options.

It is known in the art to monitor a subject's eyes, such as to measure "PERCLOS" (Percent Eyelid Closure). PERCLOS is a measure of the proportion of time that a subject's eyes are closed and generally is defined as the proportion of time that a subject's eyes are closed either completely or beyond a predetermined point over a specified period. For example, PERCLOS may be the measure of the proportion of time that a subject's eyes are between 80% and 100% closed. Often, the measurement of PERCLOS must be done manually, such as by videotaping the subject, reviewing the tape, and measuring the subject's PERCLOS. Such a method, of course, may not be practical for many applications.

Another method of determining PERCLOS involves the use of an image sensor, such as a video camera, and image processing software to monitor the subject, determine the location of the subject's eyes, and determine the subject's PERCLOS. That method, however, is time consuming and often cannot be performed in real time, thereby prohibiting it from being used to determine the drowsiness of a driver of a motor vehicle. One attempt to overcome that problem is to monitor only a portion of the subject's face, the portion containing the subject's eyes, thereby reducing the amount of processing required to determine PERCLOS. That approach, however, creates another problem. The problem arises because the subject's eyes must be tracked as they move to monitor the road and as the subject's head and body move. Often, however, the subject moves quickly and the subject's eyes cannot be tracked. As a result, the prior art devices must search for the subject's eyes and, until the subject's eyes are located, the prior art devices cannot determine PERCLOS.

Another deficiency with various aspects of the prior art, regardless of whether the subject's entire face or only the subject's eyes are monitored, is that some prior art devices have difficulty finding and monitoring the subject's eyes. For example, the prior art devices may not be able to distinguish between the subject's eyes and other sources of light and reflected light, such as is caused by dashboard lights, lights from other vehicles, and street lights. Those problems may be exaggerated when the subject is wearing glasses.

Another method for determining PERCLOS involves monitoring the eyes and entire face of a subject in real time and is insensitive to other sources of light. A method and apparatus of monitoring a subject's eyes having such features is described in U.S. Pat. No. 6,082,858 to Grace et al., which is incorporated herein by reference in its entirety.

BRIEF SUMMARY OF THE INVENTION

The present invention, in one embodiment, is directed to a device for monitoring a subject and providing feedback thereto, comprising a source of light having first and second wavelengths wherein the first wavelength does not equal the second wavelength; at least one image sensor producing a first signal indicative of reflected light having the first wavelength and a second signal indicative of reflected light having the second wavelength; a controller receiving the first and second signals and producing a third signal indicative of the first signal subtracted from the second signal; an interface in communication with the controller providing informational content to the subject in response to the third signal, wherein the informational content is associated with a behavior of the subject.

In another embodiment the present invention is directed to a method, comprising: directing light having a first wavelength toward a subject; directing light having a second wavelength toward the subject, wherein the first wavelength does not equal the second wavelength; capturing a first image of light reflected by the subject having the first wavelength; capturing a second image of light reflected by the subject having the second wavelength; subtracting a signal indicative of the first image from a signal indicative of the second image and producing a third signal; and providing informational content to the subject in response to the third signal. In another embodiment the present invention is directed to a device for monitoring a subject and providing feedback thereto, comprising: a monitoring device for providing a signal indicative of the subject's behavior; and an interface in communication with the monitoring device for providing informational content to the subject in response to the signal.

In another embodiment the present invention is directed to an apparatus, comprising: an interface for receiving a signal associated with a subject's state of drowsiness; and a feedback device in communication with the interface for providing informational content to the subject in response to the signal; wherein the informational content includes information associated with the subject's behavior while in the state of drowsiness; and wherein the informational content is presented in a form that facilitates the subject's decision making process.

In another embodiment the present invention is directed to a method, comprising: monitoring a subject's behavior; producing a signal indicative of the subject's behavior; and providing informational content to the subject in response to the signal.

In another embodiment the present invention is directed to a method, comprising: receiving a signal associated with a subject's state of drowsiness; and providing informational content to the subject in response to the signal; wherein the informational content includes information associated with the subject's behavior while in the state of drowsiness; and wherein the informational content is presented in a form that facilitates the subject's decision making process.

BRIEF DESCRIPTION OF THE SEVERAL VIEWS OF THE DRAWING

For the present invention to be clearly understood and readily practiced, the present invention will be described in conjunction with the following figures, wherein:

FIG. 1c is an image resulting from the image of FIG. 1b being subtracted from the image of FIG. 1a;

DETAILED DESCRIPTION OF THE INVENTION

Figure 1:
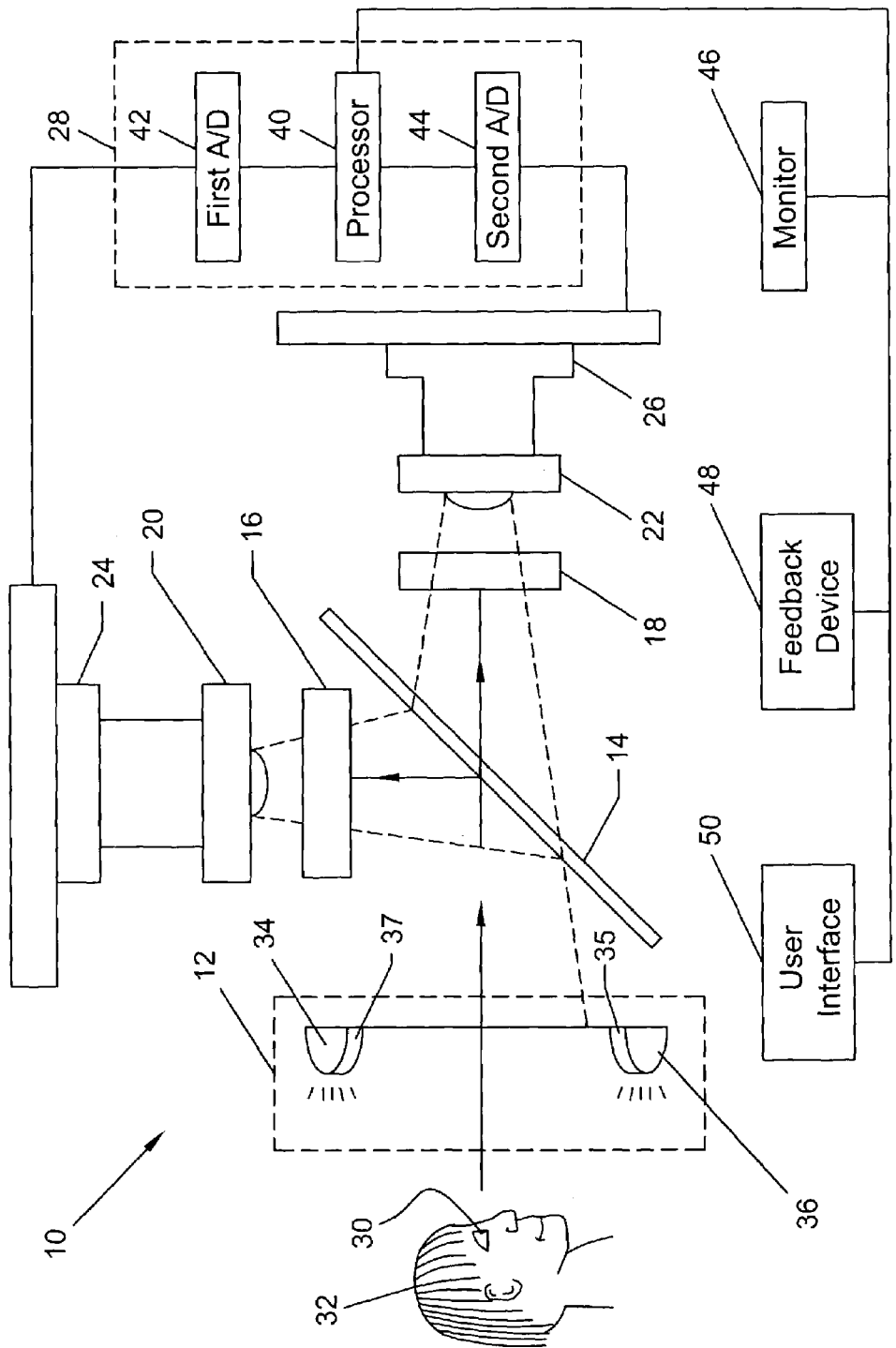
FIG. 1 is a combination block diagram and circuit schematic of a device constructed according to the present invention.

One embodiment of the present invention provides an apparatus and method for monitoring a subject and providing feedback to the subject. The monitoring apparatus may include any device capable of monitoring the subject's state of drowsiness or alertness such as, for example, ocular measurements that can be used as an indicia of drowsiness, fatigue, alertness, and the like. Other monitoring devices may include facial scanning devices, cameras, infrared scanners, and other devices that also are capable of providing indicia of the subject's state of drowsiness, fatigue, or alertness and are capable of measuring PERCLOS.

A variety of methods are used to measure drowsiness or sleepiness. Eyelid closure can be measured using camera-based systems, for example. Camera based systems include using a single camera or a single camera with an illumination source for nighttime operation. Nissan, for example, has reported such a system. SeeingMachines uses a stereo camera system to measure eyelid closures. The rate of eyelid closure can also be identified by these systems and can be used to indicate drowsiness. Millimeter wave electromagnetic sensors also have been proposed for measuring eyelid closures. Sensors attached to a person's glasses or a person's face also have been used to measure eye closures, head movements, and head nods also have been considered for measuring drowsiness. A variety of sensors also can be used to identify head movement. For example, capacitive array sensors have been successfully installed in headliners for this purpose. Mercury switches attached to a subject's ear have also been used. Drowsiness also can be measured indirectly by monitoring driver performance. AssistWare, for example, offers a device that measures the driver's ability to track a driving lane. Several authors have proposed using steering wheel movements to measure drowsiness. These methods generally may include sudden abnormal steering wheel movements and a lack of normal steering wheel movements. Dinges and Mallis have reported that over 120 methods have been reported for detecting drowsiness.

The scope of the present invention, however, is not limited to any particular type of monitoring device and the present invention may employ any apparatus that is capable of measuring the subject's state of drowsiness, fatigue, or alertness that provides an electrical signal or computer readable information as indicia of such a state.

Furthermore, one embodiment of the present invention provides feedback to the subject in response to the measured indicia of drowsiness, fatigue, or alertness in the form of one or more alerting stimuli. For example, a feedback device in accordance with one embodiment of the present invention may provide a first audible, visual, or tactile alarm or stimulus to the subject to seize the subject's attention in conjunction with, or following shortly thereafter, a second audible, visual, or tactile alarm or stimulus to provide the subject with informational content related to his state of drowsiness, fatigue, or alertness such that the subject may make an informed decision based on the informational content.

A further description of the present invention will now be deferred pending a brief description of an apparatus illustrated in FIG. 1, which may be employed by one embodiment of the present invention for monitoring a subject's state of drowsiness, fatigue, or alertness, such as measuring PERCLOS and providing feedback to the subject in accordance with the subject's state.

Accordingly, in one embodiment the present invention may utilize an ocular scanning device that measures a subject's eye using two or more different wavelengths of light. Such device will be described in terms of two different wavelengths of light, although more than two wavelengths may also be used. Generally, light is reflected by the different components of the eye. In the light spectrum, however, there are peaks and valleys in the reflection/absorption characteristics. Some wavelengths of light, such as about 850 nm, are largely reflected, while other wavelengths demonstrate significant absorption. One wavelength in particular, about 950 nm, is largely absorbed. It has been found that by using light having two different wavelengths, with each wavelength having different reflection/absorption characteristics, useful measurements, such as PERCLOS, can be obtained. It also has been found that two wavelengths, about 950 nm and about 850 nm, are particularly useful in that regard, although other wavelengths may provide superior results. Aside from the significantly different retinal reflection/absorption characteristics of 950 nm light and 850 nm light, however, they produce images of a human face that are nearly identical. As a result, two images formed from light of 950 nm and 850 nm, respectively, are approximately identical to each other except that the image formed from light having a wavelength of about 950 nm will not have an image (or will have a very faint image) of the subject's pupils.

The wavelengths of 950 nm and 850 nm are only an example of two wavelengths that may be used in a monitoring device 10 in conjunction with the present invention, and are not to be construed as limitations of the invention. Other wavelengths, having different reflection/absorption characteristics, also may be used. As a general guideline, it may be desirable that the light used not be pupil restricting, not be damaging to the subject, and not be distracting (e.g., not visible to the subject). Infrared light generally is a good choice, although other wavelengths also may be used. The extent to which the reflection/absorption characteristics of two wavelengths must differ for use with the present invention may depend on the sensitivity of the equipment being used. Furthermore, although the retina generally provides the greatest variance of reflection/absorption, the other parts of the eye, such as the lens, vitreous, and the aqueous portions, also exhibit reflection/absorption characteristics that may be used with the present invention. Although the subject monitoring device 10 in accordance with the present invention will often be described with respect to the retina and infrared light, the present invention may be used with the other portions of the eye and with other wavelengths.

The present invention may be used in many ways, including determining PERCLOS and as a gaze tracker. The present invention has many applications, including use in automobiles to reduce the risk that the driver will fall asleep at the wheel. Another application is in commercial motor vehicles, such as large trucks and vehicles carrying hazardous materials. The present application may also be used for paraplegic communications and human factors studies. The present invention will be discussed with respect to determining PERCLOS, although one of skill in the art will understand from that description that the present invention has many other applications.

In one embodiment the present invention provides a monitoring device 10 that measures slow eyelid closures as represented by PERCLOS which has been separately validated in two independent laboratories as an accurate predictor of performance degradation in sleep deprived subjects. In one embodiment of the present invention, the monitoring device 10 may be a video-based system for measuring the subject's slow eyelid closure. The monitoring device 10 may use a structured illumination approach for identifying the subject's eyes, for example. The video-based system approach obtains two consecutive images of a subject, such as a driver in a motor vehicle, using a single camera. A first image is acquired using an infrared illumination source at 850 nm that produces a distinct glowing of the subject's pupils (the red-eye effect). A second image uses a 950 nm infrared illumination source that produces an image with dark pupils. These two images are identical except for the brightness of the pupils in the image. A third image enhances the bright eyes, calculating the difference of these two images. The subject's eyes are identified in the third image by applying a threshold to the pixel brightness. This process is discussed in more detail hereinbelow.

FIG. 1 is a schematic drawing illustrating a monitoring device 10 for monitoring a subject constructed according to one embodiment of the present invention. The monitoring device 10 includes a light source 12, a beamsplitter 14, first and second filters 16, 18, first and second lenses 20, 22, first and second image sensors 24, 26, and a controller 28. The device 10 may be used to monitor the eyes 30 of a subject 32.

The light source 12 in one embodiment produces at least two wavelengths of light. The first wavelength may be, for example, about 950 nm, and the second wavelength may be, for example, about 850 nm. The source of light may be formed from a plurality of light emitting diodes ("LED"s) 34, 35. For example, one LED 34 may produce a wavelength of light of about 950 nm, and the other LED 35 may produce a wavelength of light of about 850 nm. The source of light 12 may include a plurality of LEDs 34–37 producing each wavelength of light, such as two LEDs 34, 36 producing a wavelength of light of about 950 nm, and two LEDs 34, 37 producing a wavelength of about 850 nm. It can be understood that more than two LEDs 34–37 for each wavelength also may be used. The LEDs may be formed in a ring so that light produced by the LEDs 34–37 is incident upon and reflected by the eye 30, and the reflected light passes through the ring formed by the LEDs 34–37, as illustrated in FIG. 1. The light source 12 may produce both the first and second wavelengths at about the same intensity, or it may produce one wavelength at a higher intensity than the other, such as to compensate for insensitivity of one of the wavelengths. An eye 30 tends to reflect light at approximately the same angle at which the light is incident onto the eye 30. As a result, the reflected light tends to follow a path that is very similar to the path of the incident light. Accordingly, the light source 12 may be positioned close to and around a desired path into the device 10 for the reflected light, so that there is only a small angle between the incident light and the reflected light.

The beamsplitter 14 may be, for example, a 50/50 beamsplitter tuned to direct about half of the reflected light into the first filter 16, and about half of the reflected light into the second filter 18. Beamsplitters 14 that are other than 50/50 beamsplitters may also be used, such as if it is desired to provide more of the reflected light to one of the first and second filters 16, 18. The beamsplitter 14 may be, for example, a metallized beam splitter. The beamsplitter 14 also may be a dichroic beamsplitter. A dichroic beamsplitter may be more efficient than a metallized beamsplitter, thereby making more light available for processing and requiring less light for proper operation.

The first and second filters 16, 18 pass light of the first and second wavelengths, respectively. For example, the first filter 16 may pass light with a wavelength of about 950 nm, and the second filter 18 may pass light having a wavelength of about 850 nm. As a result, the first and second filters 16, 18 provide that only selected light is passed to the lens 20, 22 and the image sensors 24, 26. The first and second filters 16, 18 may be, for example, dielectric filters, and may have a 50 nm half power bandwidth.

The first and second lens 20, 22 focus the light passing through the first and second filters 16, 18, respectively, so that a clear image may be received by the first and second image sensors 24, 26. The first and second lens 20, 22 may be separate elements of the device 10 or they may be integral to the first and second image sensors 24, 26.

The first and second image sensors 24, 26, receive the light focused by the first and second lens 20, 22, respectively. The first and second image sensors 24, 26 provide first and second signals, respectively, that are indicative of the images received by the image sensors 24, 26. The first and second image sensors 24, 26 may be, for example, charge coupled devices ("CCD") or CMOS-type devices.

To facilitate the production of more identical images from the first and second image sensors 24, 26, the image sensors 24, 26 may be synchronized using a common synchronization signal, such as may be provided by the controller 28, so that each frame or image from the first image sensor 24 is taken at the same point in time as an image from the second image sensor 26. In other words, the synchronization signal facilitates the production of a pair of corresponding images, one from the first image sensor 24, and the other from the second image sensor 26, both taken at the same point in time. As a result, differences due to changes in the subject 32 with time, such as changes in expression and movement of the subject 32, may be eliminated.

One embodiment of the present invention utilizes the fact that light reflected from the subject's retina returns along the same path as the incident light from the light source. As a result, retinal reflection will be available to a fixed device 10 (such as a device 10 fixed on an automotive dashboard), even when the subject is looking over a wide range of angles. It has been found that reflected light is available over a range of incident beams as much as about 70 degrees off axis.

The controller 28 receives first and second signals from the first and second image sensors 24, 26, processes those signals, and produces a signal indicative of that processing. The controller 28 may include a processor 40, such as a Pentium® PC104 ("Pentium" is a registered trademark of Intel Corporation, Santa Clara, Calif.). If the first and second image sensors 24, 26 provide an analog output signal, as opposed to a digital output signal, first and second analog-to-digital converters 42, 44 may be provided to convert the output signals from the first and second image sensors 24, 26, respectively, to digital signals for use by the processor 40. If the processor 40 does not require a digital signal, the converters 42, 44 may be omitted. The controller 28 may provide one or more of the first, second, and third signals to a video monitor 46 to display one or more images represented by those signals. The controller 28 also may provide a signal to a feedback device 48 if the subject is determined to be drowsy.

In one embodiment of the present invention the feedback device 48 provides a first signal that may be an audible, visual, olfactory, or tactile alarm or stimulus to seize the subject's attention in response to the signal from the controller 28. Furthermore, in conjunction with the first signal, or following shortly thereafter, the feedback device provides a second signal that may be an audible, visual, olfactory, or tactile alarm or stimulus. The second signal, however, provides the subject with informational content related to his state of drowsiness, fatigue, or alertness. In one embodiment, the information is pertinent to a driver's driving performance and safety, e.g., how far the driver drove with his/her eyes closed. The information conveyed by the second signal, therefore, promotes situational awareness and promotes proper decisions by the driver. Accordingly, such informational content-based feedback to the subject also can assist the subject, e.g., a driver, in making an informed decision such as determining the best time to stop and rest and can encourage the subject to stop and rest using one of a number of napping strategies or fatigue management techniques that are well known in the art. Furthermore, such informational content based feedback also provides the subject with an opportunity of evaluating or achieving a certain level of understanding of his or her own fatigue along with the consequences of engaging in potentially dangerous activities, such as driving while in a drowsy or fatigued state. The informational content based feedback approach according to one embodiment of the present invention also provides guidance to the subject with regard to managing fatigue.

Figure 1A:
FIG. 1a is an image of a subject illuminated with a light having a wavelength of about 950 nm.
Figure 1B:
FIG. 1b is an image of a subject illuminated with a light having a wavelength of about 850 nm.
Figure 1C:
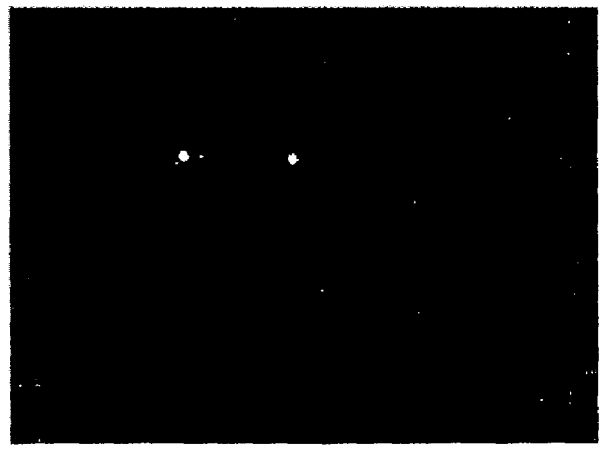
Figure 2:
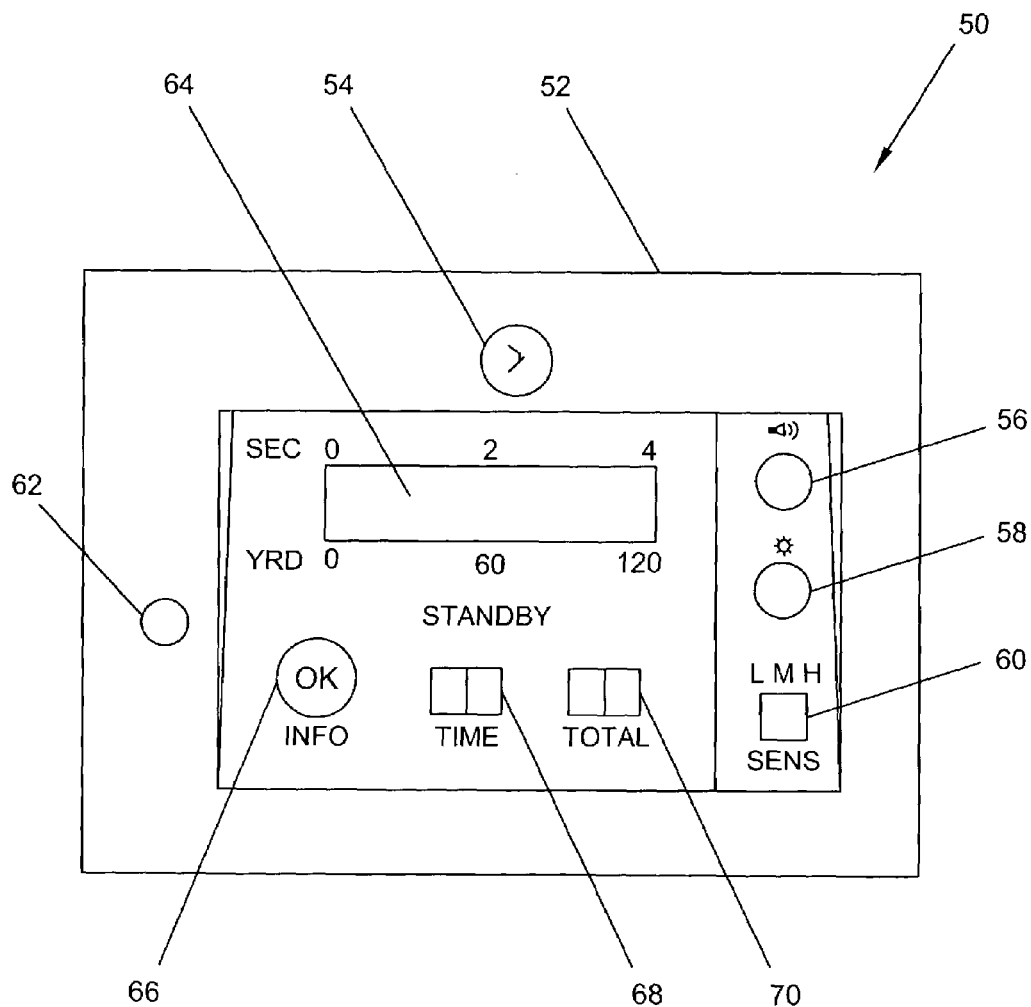
FIG. 2 is a block diagram of an interface device constructed according to the present invention.

The three images used by the monitoring device 10 are shown in FIGS. 1a–1c. One example of a bright-eye image is illustrated in FIG. 1a and one example of a dark-eye image is illustrated in FIG. 1b. The bright-eye image and the dark-eye image are essentially identical except for the glowing pupils in the bright eye image. The difference-image, illustrated in FIG. 1c, eliminates all image features except for the glowing pupils.

FIGS. 1a–1c will now be discussed in further detail to aid in understanding the operation of one embodiment of one monitoring device 10 that may be used in conjunction with the present invention. Accordingly, FIGS. 1a and 1b illustrate examples of first and second images of the subject 32 produced by the first and second image sensors 24, 26. FIG. 1a is an image of the subject 32 formed from light having a wavelength of about 950 nm, and FIG. 1b is an image formed from light having a wavelength of about 850 nm. FIGS. 1a and 1b are the same except that the intensity of light reflected by the retina is significantly different due to the different absorption characteristics of 950 nm light and 850 nm light.

In operation, the light source 12 produces light that is incident on the subject's eye 30. The distance between the light source 12 and the subject's eye 30 will vary depending on the particular application, but an exemplary distance is about three feet. That light is reflected back to the device 10 and is split by the beam splitter 14. Part of the split light is directed towards the first filter 16, and that light is filtered by the first filter 16, focused by the first lens 20, and received by the first image sensor 24. Another part of the split light is directed towards the second filter 18, and that light is similarly filtered by the second filter 18, focused by the second lens 22, and received by the second image sensor 26. The first and second image sensors 24, 26 produce first and second signals, respectively, indicative of the images received by those image sensors 24, 26. The first and second signals are provided to the controller 28, wherein the first and second analog-to-digital converters 42, 44 convert the first and second signals from analog signals to digital signals, and provide those digital signals to the processor 40. The processor 40 subtracts one of the images, represented by one of the first and second signals, from the other of the images, represented by the other of the first and second signals, to produce a third image. Because the first and second images may be, at least for practical purposes, the same except that one of the images should include an image of the retina while the other may not include an image of the retina (or may include a more faint image of the retina), when one of the images is subtracted from the other to produce the third image, the third image may be an image of only the retina of the subject 32. The subtraction of one image from the other may be done, for example, by comparing corresponding pixels of each of the first and second images, and determining the state of the corresponding pixel in the third image. For example, if the corresponding pixels in both the first and second images is the same, either on or off, then the corresponding pixel in the third image should be off. If, however, the pixels are different, then the corresponding pixel in the third image should be on.

One embodiment of the present invention utilizes a property of the eye 30 to measure PERCLOS. Further, in one embodiment the present invention utilizes a differential reflection intensity property of the eye. In particular, in one embodiment the present invention utilizes the fact that the eye 30 will generally absorb light at a wavelength of about 950 nm, and the eye, more specifically the retina, will generally reflect light at other wavelengths, such as about 850 nm. One embodiment of the present invention illuminates the subject's eyes 30 with both frequencies of light at appropriate intensities to produce similar images, measures the reflected image at each of the wavelengths, subtracts one of the images from the other to form a third image that is primarily only of the subject's pupils. From the third image, the present invention can determine whether and to what extent the subject's eyes 30 are open (or closed). Because the third image contains much less data than a normal image of the subject, it can be processed more easily and more quickly than a conventional image of the subject.

The present invention has many applications. For example, the measure of PERCLOS is recognized by the United States Department of Transportation as the most effective means of measuring driver drowsiness. See, for example, the report to the National Highway Traffic Safety Administration, at the United States Department of Transportation, entitled Evaluation of Techniques for Ocular Measurement as an Index of Fatigue and as the Basis for Alertness Management, dated Apr. 1, 1998, by David F. Dinges, Ph.D, Melissa Mallis, Greg Maislin M. A., M. S., John Walker Powell, IV, M. A., which is incorporated herein by reference. In such an application, the present invention offers a significant advantage because, (generally and in many applications) to be effective, determining the alertness (or drowsiness) of a driver must be done in real time.

FIG. 1c is an example of the third image produced by the controller 28. FIG. 1c illustrates only the subject's retinas. The third image is indicative of whether the subject's eyelids are closed, as well as the degree to which the subject's eyelids are closed.

In one embodiment of the present invention the subject is a driver and is to be monitored in real time while operating a vehicle. Accordingly, the monitoring device 10 may be housed in a housing suitable for mounting on a surface of the vehicle. For example, the monitoring device 10 may be mounted in an interior portion of the vehicle. Further, the monitoring device 10 may be mounted in a housing suitable for mounting on a dashboard of the vehicle or, more specifically, may be mounted in a housing suitable for mounting on a dashboard of the vehicle just to the right of the steering wheel. The monitoring device 10 may be equipped with one or more degrees-of-freedom and a rotating base to allow the driver to adjust the monitoring device 10. In one example, the monitoring device 10 may be equipped with rotating base having two degrees-of-freedom. Dashboard styles vary in their depth and the angle at which they slope back toward the windshield. Accordingly, the mounting mechanism can be made adaptable while at the same time should provide enough stability to avoid excessive vibration. Also, the mounting mechanism is securely affixed to the dashboard to prevent the monitoring device 10 separating from the dashboard in the event of a collision or sudden stopping.

The monitoring device 10 may include a housing having a front face resembling the shape of a rear view mirror, for example. The driver may be instructed to adjust the aim of the monitoring device 10 holding it as if he/she would a rear view mirror. The monitoring device 10 may be properly adjusted when the driver can see his/her reflection in the front face. The field of view may be large enough to accommodate significant head movement. For example, at a distance of 30 cm from the monitoring device 10, a square image measuring 30 cm is obtained. This image size allows approximately 42 cm of head translation while maintaining at least one eye in the field of view.

One embodiment of the present invention provides an integral driver interface 50, which may include one or more visual, audible, olfactory, and tactile alarm or stimulus feedback devices 48 to convey informational content to the driver. In one example, the present invention provides a driver interface 50 having a visual gauge and an audible advisory tone. The visual gauge may employ one or more Light Emitting Diodes (LEDs). In one embodiment the visual gauge may employ six LEDs, which may be color coded to represent varying levels of drowsiness, fatigue, or alertness. In one embodiment, the first three LEDs may be amber, representing moderate drowsiness levels, while the second three LEDs may be red, representing severe drowsiness. Such a scale may be calibrated to represent PERCLOS calculated over a 3-minute period, for example. Accordingly, the first amber LED may be calibrated to correspond to P3=0.08, while each additional LED may be calibrated to correspond to an increase of 0.02, for example. Hence, a moderately drowsy range would correspond to 0.08<P3<0.14 and the a severely drowsy range corresponds to P3>0.14.

One embodiment of the driver interface 50 in accordance with the present invention includes a visual, audible, olfactory, or tactile feedback device 48 to alert the driver and give the driver an opportunity to grasp additional informational content relating to his/her state of drowsiness, fatigue, or alertness provided by the driver interface 50. For example, the feedback device 48 may first provide an auditory advisory tone that is simultaneously or substantially simultaneously reinforced by informational content provided on a second visual gauge that relates to driver performance and safety. These two indicators are presented to the driver in a way that is intended to encourage the driver to take actions to increase his or her alertness or to stop and rest. In one embodiment of the present invention the feedback device may include a transducer that produces an advisory tone in the audible frequency band. For example, the audible indicator may be a transducer that is commonly used in automobiles that generates an audible advisory tone at a standard 3000 Hz when it is energized. In one embodiment of the present invention, the audible advisory tone may be actuated when the first amber LED is lit and again when the first red LED is lit. The audible advisory tone also may be programmed to trigger periodically when drowsiness is in the yellow, moderately drowsy, or red, severely drowsy, regions, for example. Those skilled in the art will appreciate that the scope of the invention is not limited to providing an audible advisory tone as feedback in order to grab a driver's attention that may have dozed off for a brief period. Other feedback devices may include, among others, tactile devices that vibrate and thus cause the driver to be alerted or olfactory devices that emit a certain smell in order to alert the driver. Furthermore, other feedback devices may include sources of heat, cold air, intense lights concentrated in a defined area, and the like, an may be subject to the limitation that such feedback devices merely alert the drowsy driver and do not startle the driver. One purpose of all such feedback devices is to alert a drowsy driver that may have dozed off so that the driver may come to realize his/her state of drowsiness, fatigue, or alertness by observing a secondary feedback device that provides informational content related thereto.

One embodiment of the present invention will now be described with respect to a specific example in which the invention may be practiced. The specific example, however, should not be construed as limiting the scope of the present invention thereto or in any manner and is merely provided to help illustrate one specific embodiment of the present invention. Accordingly, the interaction and interface aspects of the present invention incorporate the driver's desire for a stimulating and alerting feedback with a response that encourages safe behavior. In one embodiment the present invention facilitates driver acceptance by giving the driver control over various aspects of the driver interface 50. For example, the driver may adjust the sensitivity of the drowsiness warning, select sounds that range from a robust alerting sound to a gentle advisory tone, adjust the volume to match the ambient sound environment, and/or disable the warning system should he/she find it bothersome.

Driver behavior may be addressed primarily by monitoring the driver's state of drowsiness, fatigue, or alertness and then providing the driver with informational content that alerts the driver as to the adverse effects of such state on driving. The driver interface 50 provides an informational warning display to alert the driver of the immediacy and danger of a particular situation. From the driver's perspective, the driver interface 50 is not a system that promotes alertness but rather is a fact-based drowsiness information system to assist the driver in making an informed and educated decision.

The informational display provided in the feedback device may be easily understood in the context of the concept of learnability. For example, the first experience of a novice user of a system is that of learning to use the system. By removing the obstacle of having to learn the system in the driver's first experience or decreasing the learning curve, what remains is the potential that drivers will learn to heed the warning provided by the feedback device 48 rather than having to learn to interpret the warnings.

In one embodiment of the present invention, the driver interface 50 includes a display that provides clear, easily understood measures for the drivers that potentially may be unsettling. The unsettling nature of the information will, thus, encourage the drivers to stop and rest when experiencing drowsiness, fatigue, or certain levels of alertness that are not conducive to safe driving.

Interaction and Interface

Actions taken by the driver or initiated by the monitoring device 10 are accounted for in the interaction between the driver and the monitoring device 10. The interaction may result in a visible change to the state of the driver interface 50 and may sometimes result in an underlying change that is not visible to the user. For illustration purposes only, the driver interface 50 may be thought of as a means through which a driver can interact with the monitoring device 10 in a prescribed or semi-prescribed manner and that any action taken by the driver may result in feedback from the system.

Figure 3:
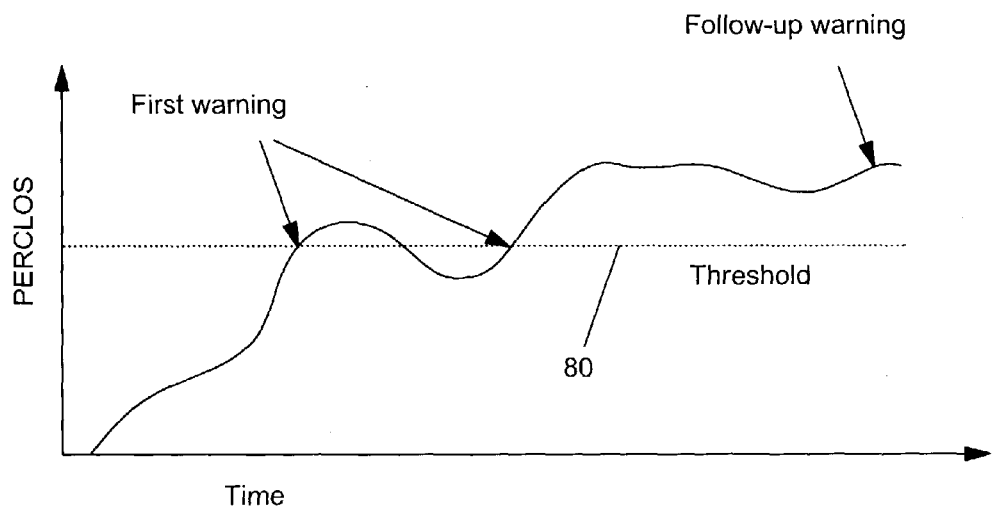
FIG. 3 is a warning diagram of a frequency mode of operation of a device according to the present invention.

An interaction flow model may be used to illustrate the high-level architecture of the driver interface 50 according to one embodiment of the present invention. The following description of one embodiment of the present invention assumes that the driver has already triggered the informational warning display of the driver interface 50. FIG. 3 illustrates a diagram of one embodiment of the driver interface 50.

In one embodiment of the present invention, the interface device 50 utilizes the front, top, and sides of a housing 52 that is suitable for mounting within a vehicle. For example, the housing 52 of the driver interface 50 may be mounted on a dashboard of the vehicle. One example of an implementation of the driver interface 50 provides a housing 52 having a height of about 5.43 inches, a width of about 4.08 inches, and a depth of about 6.12 inches. These dimensions, however, are not intended to limit the scope of the present invention and are provided for illustration purposes only. In one embodiment, the interface device 50 may include a monitoring device 10, such as a camera or image sensor, mounted on the back of the housing 52. In one embodiment of the present invention, the monitoring device 10 may include a ball and socket joint arm mount having an adjustable tension to ensure stability.

In one embodiment of the present invention the driver interface 50 may include one or more functional controls for controlling sound selection 54, volume 56, brightness/dimness 58, sensitivity 60, and standby 62 mode with system feedback for the driver. In one embodiment of the present invention the functional controls may be clustered together in accordance with the Gestalt theory for grouping information. According to the Gestalt theory, by applying design principles such as proximity, similarity, continuity, size, shape, color, labeling, positioning, etc., like controls may be grouped to the extent that the size of the driver interface 50 permits.

Furthermore, the driver interface 50 includes a display 64, an acknowledgement control button 66, and first and second secondary information displays 68, 70 for displaying elapsed time since a prior warning and the total number of warnings received, respectively. In one embodiment of the present invention, the display 64 may include a bar graph LED display with parallel legends at the top and bottom. The legends may provide scaled units of measure such as time and distance, for example. Units of distance may be selected such as to convey to the driver, at a glance, an accurate perception of distance traveled while in a drowsy state. In one embodiment of the present invention yards may be chosen as the units of distance under the assumption that many drivers are generally more familiar with yards rather than meters. Accordingly, the scaled units of time may be up to 4 seconds and the scaled units of distance may be up to 120 yards, for example, such that at a glance the driver can see the scale and easily comprehend the information being conveyed. In one embodiment of the present invention, a speed of 61 mph is assumed for converting time to distance. Furthermore, fractions of a mile and feet may not be as desirable to use as yards because the values they convey are not impressive enough or may be too large to convey an accurate perception of distance traveled while in a drowsy state. The scale of 120 yards is also fortuitously close in size to an American football field—a dimension many potential users are likely to be familiar with and would provide an effective comprehensive representation of distance traveled. To stop the warning sound the driver may push the acknowledgement control button 66 (e.g., the OK button). This in turn may trigger the secondary information displays 68, 70 that provide to the driver additional information such as the total amount of elapsed time since the previous warnings in the first secondary display 68 and the total number of warnings received in the second secondary information display 70. In one embodiment of the present invention, the secondary information may be accessible only after a first warning has been issued by the driver interface 50 and may include a time-out of 10 seconds, for example.

The informational warning display 64 or "advisor" portion of the interface 50 gives the driver valuable information in terms that emphatically point out the inherent danger in driving while drowsy. Drivers often convince themselves that—"my eyes where closed for just a second" while research shows that eye closures of 3–30 seconds have been observed. Accordingly, by displaying eye closure times, together with the total distance traveled with eyes closed, the driver will be convinced that he/she is driving in an unsafe manner and make the choice to stop and rest. The secondary warning display of how many warnings have been received 70 and the time elapsed since the last warning 68 reinforces this message.

In one embodiment of the present invention, the system may be powered by the vehicle's ignition when the user starts the vehicle, for example. In one embodiment, however, the system begins to operate only after a light sensor detects that the ambient conditions are substantially dim. Also, in one embodiment, the system begins operating only when the vehicle is in motion and the vehicle reaches or exceeds a predetermined speed such as 35 mph, for example. Those skilled in the art will appreciate, however, that the scope of the invention is not limited to any specific selection of speed.

In one embodiment of the present invention, when the driver starts the vehicle, the monitoring device 10 goes into a standby mode and the driver interface 50 illuminates a standby indicator light 72. In one example, the standby indicator light 72 is illuminated in dim red while other areas of the feedback interface device 50 remain darkened, as those areas are not illuminated at this time.

In one embodiment of the present invention the monitoring device 10 activates when conditions are dim enough to begin a PERCLOS measurement and the vehicle speed exceeds 35 mph. At such time, all of the functional controls 54–62 become available to the driver and the PERCLOS measurements begin. The standby indicator light 62 dims, an operational notification sound briefly plays, and the functional controls 54–62 are activated and become accessible to the driver. In one embodiment of the present invention, all of the functional controls 54–62 are illuminated in green while other areas of the driver interface 50 are not illuminated at this time.

The standby control 62 is separate from the other functional controls 54–60 because it may be used to disable the monitoring device 10. Positioning the standby control 62 separately reduces the chances of the driver accidentally disabling the monitoring device 10 or driver interface 50. The Adjust Brightness/Dimness control 58 affects the functional controls 54–62 that are illuminated in green. It does not, however, control the illumination of the warning display 64. Each functional control 54–62 provides the driver with feedback information according to Table 1.

TABLE 1

Control Feedback

| USER CONTROL | SYSTEM FEEDBACK |
| --- | --- |
| Adjust Volume 56 | Tactile, Auditory |
| Adjust Bright/Dim 58 | Tactile, Visual |
| Select Sound 54 | Tactile, Auditory |
| Select Sensitivity 60 | Tactile, Visual |
| Push Standby 62 | Tactile, Visual |

In one embodiment, the driver interface 50 according to the present invention provides a trigger informational warning display 64. The warning display 64 is activated, for example, when the driver exceeds the threshold for PERCLOS such as when the driver's drowsiness, fatigue, or alertness cross a predetermined threshold level of drowsiness. Accordingly, once the driver's measured PERCLOS crosses the predetermined threshold, the display 64 goes into informational warning mode and the driver interface 50 locks out the functional controls 54–62 such that the driver can no longer adjust them until a primary informational warning is acknowledged by the driver. In one embodiment of the present invention, reducing the speed of the vehicle to below the activation threshold, e.g., 35 mph, will not place the driver interface 50 into standby mode until the primary informational warning is acknowledged by the driver. Accordingly, at such time the informational warning display 64 and the corresponding acknowledgement control button 66 are illuminated in bright red while other areas are not illuminated.

The activation of the warning sound may occur simultaneously or substantially simultaneously (i.e., within a relatively short time of each other) with the activation of the informational warning display 64. Eye closure information is translated into distance traveled and the length of time that the driver's eyes were closed, for example, and are displayed on the display 64. For the purposes of the display 64, the longest single eye closure observed during the integration period is displayed. This measure is displayed rather than the PERCLOS because it is less abstract, more believable, and more relevant to the drivers' experiences. The present invention, however, should not be limited to the particular type of displayed informational content and PERCLOS. Any informational feedback content may be provided to the driver by way of the display 64 as long as it conveys to the driver that his/her eyes remained closed for a certain period and that the vehicle traveled a corresponding distance during that period to impress upon the driver that he or she is behaving in unsafe manner and to encourage the driver to get some rest.

Once the first alarm warning is activated, the driver must push the acknowledge control button 66 to cease the warning sound. This in turn triggers the warning display 64 that provides the informational content to the driver. Such information, however, is accessible only after the first warning has occurred and a 10-second time-out period has elapsed, for example. The secondary information that the monitoring device 10 collects is displayed as the total amount of time that has elapsed on the first secondary display 68 since the previous warnings and the total number of warnings received on the second secondary display 70.

Once the driver pushes the acknowledge control button 66 again to clear the warning display 64 or wait for the warning display 64 to time out, the functional controls 54–62 will again be illuminated and become usable. In one embodiment of the present invention, the sensitivity setting will also automatically reset itself internally to the next most sensitive setting. The driver then has the ability to manually override condition if he/she chooses to do so.

A quick summary of the acknowledge control button 66 functions is given in Table 2 along with the illumination scheme for the informational warning display 64 and the secondary information displays 68,70.

TABLE 2

OK Button Functionality

| INFORMATION-AL DISPLAYS | USER CONTROL | SYSTEM FEEDBACK | COLOR SCHEME |
| --- | --- | --- | --- |
| Primary Warning | OK | Informational warning display dims and warning sound ceases | Red |
|  |  | Info label beneath "OK" button illuminates | Yellow |
|  |  | Secondary information display illuminates | Yellow |

TABLE 2-continued

OK Button Functionality

| INFORMATION-<br>AL DISPLAYS | USER<br>CONTROL | SYSTEM FEEDBACK | COLOR<br>SCHEME |
|---|---|---|---|
| Secondary | OK | Secondary information display dims and functional controls illuminate | Green |
| | | Sensitivity setting switches to next higher setting | Green |

When the driver interface 50 is activated, the driver may choose to continue driving or pull over. With the PERCLOS measurements in active mode, the functional controls 54–62 of the driver interface 50 may be adjusted and the acknowledge control button 66 may be used to view the secondary information on the secondary displays 68,70, which remain illuminated in yellow after the first warning is issued and acknowledged, for example. While the acknowledge control button 66 does not remain illuminated, its position above the information label suggests to the user to push it in order to display this information. Other areas of the driver interface 50 may not be illuminated at this time. On the other hand, if the driver stops driving, the driver interface 50 returns to standby mode when the vehicle speed goes below 35 mph for more than one consecutive minute, for example, and powers off automatically when the vehicle is turned off.

All warnings, alarms, and/or stimulus feedback to the driver are triggered based on PERCLOS. Initial warnings are based on PERCLOS crossing a threshold. Historically PERCLOS triggers have been calculated, and validated, over periods ranging from 1-minute to 3-minutes using thresholds ranging from 8% to 12%. Shorter time periods and lower thresholds correspond to higher sensitivity for the detection of drowsiness. For example, by calculating the trigger with P=8% a driver will receive a warning if his/her eyes are continuously closed for a period up to 4.8 seconds. The time is extended up to 21.6 seconds if P3=12% is used. Table 3 shows the space of well-known PERCLOS thresholds with three selected values of P1=8%, P2=10%, and P3=12% corresponding to high, medium, and low sensitivity.

TABLE 3

Sensitivity Settings

| | First Warning Threshold | |
|---|---|---|
| Sensitivity Setting PERCLOS | PERCLOS Threshold (%) | Integration Period (min) |
| Low | 12 | 3 |
| Medium | 10 | 2 |
| High | 8 | 1 |

Once the initial warning is triggered and the driver has responded thereto, there are several ways of considering subsequent warnings. Three warning examples are described hereinbelow, although the scope of the invention should not be limited thereto. All these examples generate an initial first warning upon crossing a PERCLOS threshold averaged over a specified period ranging from 1-minute to 3-minutes (Table 3). There are variations in the examples as to when to warn drivers if they do not drop back below the first warning threshold. The three considered examples are Frequency, Episode, and Reset modes.

One embodiment of the present invention utilizes a frequency mode. A warning pattern for the frequency mode is illustrated in FIG. 3. In the frequency mode case follow-up warnings are given every X minutes while the driver's measured PERCLOS is above a first threshold 80. The parameter X can be a constant or can vary with the level of PERCLOS. Within the frequency mode, however, warnings are given only when the driver's eyes are closed so that the driver does not rapidly perceive the warning to be a false alarm. If the driver's eyes are open when the period ends, the monitoring device 10 waits for the next eye closure before emitting a new warning by way of the driver interface 50.

One embodiment of the present invention utilizes an episode mode. After a driver's PERCLOS value crosses and stays above the first threshold 80 the monitoring device 10 will monitor eye closure over long episodes. A triggering episode may be about 2 seconds, which is long enough to avoid triggering for a typical mirror or in-vehicle glance. This method emits alarms only when episodes are occurring and thus the risk of emitting an alarm when the driver's eyes are open is reduced.

Figure 4:
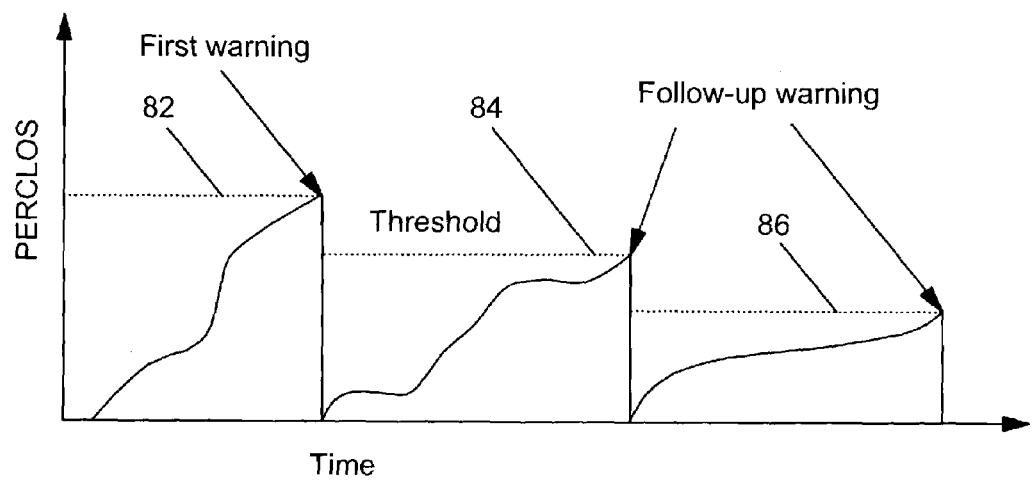
FIG. 4 is a warning diagram of a reset mode of operation of a device according to the present invention.

One embodiment of the present invention utilizes a reset mode. A warning pattern for the reset mode is illustrated in FIG. 4. After a driver's PERCLOS value crosses, and stays above, the first reset threshold 82 the system zeroes the PERCLOS calculations and sets a second reset threshold 84 at the next shortest option until it reaches the lowest level reset threshold 86. Like the episode mode, the risk of emitting an alarm when the driver's eyes are open is minimal, as the PERCLOS values must cross a threshold in a rising direction. In one embodiment of the present invention the reset mode simplifies the logic while steadily increasing the sensitivity as a drowsiness onset occurs. One feature of the reset mode is that the driver is actively engaged to the extent that he/she can override the automatic increase in sensitivity.

Figure 5:
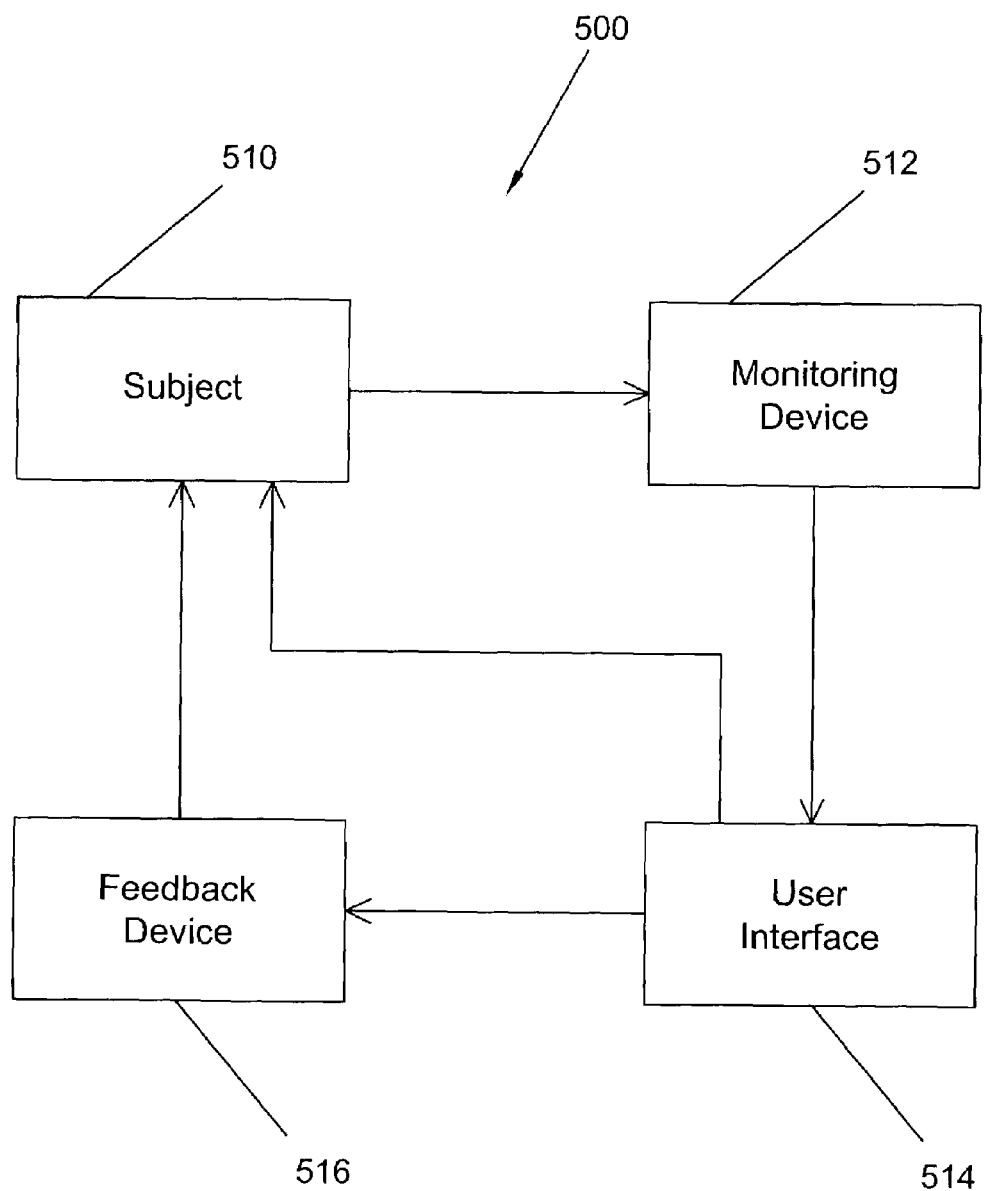
FIG. 5 is a system according to the present invention.

FIG. 5 illustrates one embodiment of a system 500 according to the present invention. The system 500 includes a monitoring device 512 for monitoring a subject 510, such as a driver operating a vehicle. The monitoring device 512 provides a signal, e.g., an electrical signal or computer readable information, to a user interface 514 device for providing informational content to the subject 510 in response to the signal from the monitoring device 512. The user interface 514 also provides information to a feedback device 516 for providing a stimulus to the subject also in response to the signal. Those skilled in the art will appreciate that the feedback device 516 and the user interface device 514 may be combined as one unit and may receive the signal from the monitoring device 512 at the same time.

Volume Settings

Guidelines for in-vehicle displays suggest a wide range of volume. For example to make it possible to hear all auditory output under all driving conditions a 50 dB(A) and 90 dB(A) range of volume may be suitable while volumes higher than 90 dB(A) may be avoided.

These guidelines, however, often fail to account for the relatively high noise levels that are present in older model trucks. Research specific to truck cab noise levels implies that many drivers are exposed to levels near or at OSHA noise exposure standards (90 dBA over 8 hours or 88.2 dBA for 10 hours). Accordingly, it may be difficult to adequately predict a comfortable range for audible warnings. As with car stereo systems and CB radios, the closest analogous interfaces in a vehicle cab, there is an expectation that a very small minority will even attempt to select the loudest volume. Thus, in one embodiment of the present invention a high upper end of the volume may be set at approximately 100 dBA and a low setting may be set at approximately 85 dBA, which is about 15 dBA above the lowest reported in-cab value of about 68.7 dBA.

Illumination Settings

Reduced levels of luminance at night may interfere with the legibility of text and icons. Accordingly, if the driver interface 50 is configured with a minimum brightness that is too low, text luminance may drop below legible threshold levels. The provision of the brightness control knob 58 should readily permit the users to identify the necessary illumination level to fit their own needs and varying levels of visual acuity. When the monitoring device 10 enters a warning state, the brightness of the driver interface 50 will be fixed to a level that is above the legible limits.

Labeling

One embodiment of the present invention provides one or more labels for the functional controls 54–62 and the warning display 64. Such labels may be a combination of commonly understood abbreviations and/or standardized international icons as shown in Tables 4 and 5.

TABLE 4

Functional Controls

| USER CONTROL | LABEL |
|---|---|
| Adjust Volume | Icon |
| Adjust Dim | Icon |
| Select Sound | Icon |
| Select Sensitivity | SENS; L, M, H |
| Push Standby | STNBY |
| Acknowledge warning | OK |

TABLE 5

Informational Displays

| DISPLAY | LABEL |
|---|---|
| Seconds | SECS |
| Yards | YDS |
| Information | INFO |
| Time | TIME |
| Total | TOTAL |

Typography

In one embodiment of the present invention, the typography for the labels is determined in accordance with basic typographic principles of legibility. General characteristics of legible typefaces include contrast, simplicity, and proportion. Furthermore, the manner in which the typefaces are used and the spatial relationships of the letter forms also contribute to the legibility. For example, using all capital letters may interfere with the readability of words and may require a larger amount of space than lowercase letters. In a darkened cab interior at a distance, however, using all capital letters may help with the readability of the labels as they take on more of a display quality. Finally, the size, inter-letter spacing (kerning), and the weight of the type also are factors that affect the legibility of the typeface. The misapplication of any of these factors may have an impact on the usability of the feedback interface device 50. In one embodiment of the present invention, a Gill Sans bold and Gill Sans Condensed bold typeface is provided to aid with the visibility of the characters. The Gill Sans typeface is a well-known highly legible typeface. Those skilled in the art will appreciate that the typeface is considered to be an informal and friendly looking typeface, which is a subtle perceptual quality that should not be underestimated when used on a device whose use may be initially resisted.

The driver interface 50 also may be most used as part of a fatigue management program that emphasizes education and safety. The goal of any fatigue management program is to minimize driver fatigue (maximize driver alertness) and, hence, maximize driver performance, which in turn maximizes both productivity and safety. The first step in implementing a fatigue management program is education. Workers, supervisors, and managers need to understand basic sleep physiology and learn to speak a common language. A fatigue management-training curriculum may take many forms. For example, the curriculum may be arranged as an overall wellness program including basic information about fatigue, good eating habits, and exercise. The basic curriculum may also be modified to include industry specific issues such as wisely applying hours of service regulations. Whatever its form, certain core information about basic sleep physiology is required. The basic information includes: (1) the basic human drive for sleep; (2) how much sleep the average person requires each day; (3) performance degradation as sleep debt accumulates; (4) circadian rhythms and their effects on fatigue and performance; and (5) fatigue management strategies—napping strategies, strategic use of caffeine etc. This basic information will provide the knowledge that a driver needs to best manage his/her sleep—wake cycle, and to understand and internalize the relationship between drowsiness and safety.

Those of ordinary skill in the art will recognize that many modifications and variations of the present invention may be implemented. The foregoing description and the following claims are intended to cover all such modifications and variations. Furthermore, the materials and processes disclosed are illustrative, but are not exhaustive. Other materials and processes may also be used to make devices embodying the present invention.

What is claimed is:

1. A device for monitoring a subject who is driving a vehicle and providing feedback thereto, comprising:
   a source of light having first and second wavelengths wherein the first wavelength does not equal the second wavelength;
   at least one image sensor producing a first signal indicative of reflected light having the first wavelength and a second signal indicative of reflected light having the second wavelength;
   a controller receiving the first and second signals and producing a third signal indicative of the first signal subtracted from the second signal such that the third signal is indicative of whether the subject is driving the vehicle while in a state of drowsiness; and
   an interface in communication with the controller providing informational content to the subject in response to the third signal, wherein the informational content includes a distance driven by the subject while driving the vehicle in the state of drowsiness.

2. The device of claim 1, wherein the interface further comprises a feedback device in communication therewith providing a first and second stimulus to the subject in response to the third signal.

3. The device of claim 2, wherein the first stimulus is selected from the group consisting of a visual, audible, olfactory, and tactile stimulus.

4. The device of claim 2, wherein the second stimulus is selected from the group consisting of a visual, audible, olfactory, and tactile stimulus.

5. The device of claim 4, wherein the second stimulus includes the informational content provided to the subject.

6. The device of claim 2, wherein the interface includes a functional control.

7. The device of claim 2, wherein the interface further comprises a visual gauge for providing informational content to the subject.

8. The device of claim 7, wherein the visual gauge provides a coded output that represents a state of the subject determined in accordance with the third signal.

9. The device of claim 8, wherein the coded output includes a color code and wherein the color code represents one or more states of drowsiness, fatigue, or alertness of the subject.

10. The device of claim 2, wherein the first stimulus is an audible stimulus and the second stimulus is a visual stimulus.

11. The device of claim 10, wherein the feedback device is for providing the first and second stimulus simultaneously.

12. A method of monitoring a subject driving a vehicle and providing feedback to the subject comprising:
    directing light having a first wavelength toward the subject;
    directing light having a second wavelength toward the subject, wherein the first wavelength does not equal the second wavelength;
    capturing a first image of light reflected by the subject having the first wavelength;
    capturing a second image of light reflected by the subject having the second wavelength;
    subtracting a signal indicative of the first image from a signal indicative of the second image and producing a third signal that is indicative of whether the subject is driving the vehicle while in a state of drowsiness; and
    providing informational content to the subject in response to the third signal, wherein the informational content includes a distance driven by the subject while driving the vehicle in the state of drowsiness.

13. The method of claim 12, further comprising providing in response to the third signal a first stimulus and second stimulus to the subject.

14. The method of claim 13, wherein providing the first stimulus includes providing the first stimulus selected from the group consisting of a visual, audible, olfactory, and tactile stimulus.

15. The method of claim 13, wherein providing the second stimulus includes providing the second stimulus selected from the group consisting of a visual, audible, olfactory, and tactile stimulus.

16. The method of claim 13, further comprising providing informational content to the subject by way of a visual gauge.

17. The method of claim 16, further comprising providing a coded output representative of a state of the subject determined in accordance with the third signal.

18. The method of claim 13, wherein the first stimulus is an audible stimulus and the second stimulus is a visual stimulus.

19. The method of claim 18, wherein the first stimulus and the second stimulus are provided simultaneously.

20. A device for monitoring a subject who is driving a vehicle and providing feedback thereto, comprising:
    a monitoring device for providing a signal indicative of the subject driving the vehicle while in a state of drowsiness; and
    an interface in communication with the monitoring device for providing informational content to the subject in response to the signal, wherein the informational content includes a distance driven by the subject while driving the vehicle in the state of drowsiness.

21. An apparatus for monitoring a subject driving a vehicle and providing feedback to the subject, comprising:
    an interface for receiving a signal associated with a state of drowsiness of the subject; and
    a feedback device in communication with the interface for providing informational content to the subject in response to the signal, wherein the informational content includes a distance driven by the subject while driving the vehicle in the state of drowsiness.

22. The apparatus of claim 21, wherein the interface includes a display.

23. The apparatus of claim 22, wherein the display is color-coded and the color is related to the subject's state of drowsiness.

24. The apparatus of claim 21, further comprising a functional control for enabling the subject to adjust a parameter associated with the interface.

25. The apparatus of claim 21, further comprising a functional control for enabling the subject to adjust a parameter associated with the feedback device.

26. A method of monitoring a subject driving a vehicle and providing feedback to the subject, comprising:
    monitoring whether the subject is driving the vehicle while in a state of drowsiness;
    producing a signal indicative of whether the subject is driving the vehicle while in a state of drowsiness; and
    providing informational content to the subject in response to the signal, wherein the informational content includes a distance driven by the subject while driving the vehicle in the state of drowsiness.

27. A method of monitoring a subject driving a vehicle and providing feedback to the subject, comprising:
    receiving a signal associated with a state of drowsiness of the subject; and
    providing informational content to the subject in response to the signal, wherein the informational content includes a distance driven by the subject while driving the vehicle in the state of drowsiness.

28. A device for monitoring a subject who is driving a vehicle and providing feedback thereto, comprising:
    a monitoring device for providing a signal indicative of the subject driving the vehicle while in a state of drowsiness; and
    an interface in communication with the monitoring device for providing informational content to the subject in response to the signal, wherein the informational content includes a length of time that the subject drove the vehicle while the subject was in the state of drowsiness.

29. The device of claim 28, wherein the interface further comprises a feedback device providing a first and second stimulus to the subject in response to the signal.

30. The device of claim 29, wherein the first stimulus is an audible stimulus and the second stimulus is a visual stimulus.

31. The device of claim 30, wherein the feedback device is for providing the first and second stimulus simultaneously.

32. A device for monitoring a subject who is driving a vehicle and providing feedback thereto, comprising:
- a source of light having first and second wavelengths wherein the first wavelength does not equal the second wavelength;
- at least one image sensor producing a first signal indicative of reflected light having the first wavelength and a second signal indicative of reflected light having the second wavelength;
- a controller receiving the first and second signals and producing a third signal indicative of the first signal subtracted from the second signal such that the third signal is indicative of whether the subject is driving the vehicle while in a state of drowsiness; and
- an interface in communication with the controller providing informational content to the subject in response to the third signal, wherein the informational content includes a length of time that the subject drove the vehicle while the subject was in the state of drowsiness.

33. The device of claim 32, wherein the interface further comprises a feedback device for providing a first and second stimulus to the subject in response to the third signal.

34. The device of claim 33, wherein the first stimulus is an audible stimulus and the second stimulus is a visual stimulus.

35. The device of claim 34, wherein the feedback device is for providing the first and second stimulus simultaneously.

36. A method of monitoring a subject driving a vehicle and providing feedback to the subject comprising:
- directing light having a first wavelength toward the subject;
- directing light having a second wavelength toward the subject, wherein the first wavelength does not equal the second wavelength;
- capturing a first image of light reflected by the subject having the first wavelength;
- capturing a second image of light reflected by the subject having the second wavelength;
- subtracting a signal indicative of the first image from a signal indicative of the second image and producing a third signal that is indicative of whether the subject is driving the vehicle while in a state of drowsiness; and
- providing informational content to the subject in response to the third signal, wherein the informational content includes a length of time that the subject drove the vehicle while the subject was in the state of drowsiness.

* * * * *